United States Patent [19]

Del Rossi et al.

[11] Patent Number: 5,196,628

[45] Date of Patent: Mar. 23, 1993

[54] LIQUID ACID ALKYLATION CATALYST AND ISOPARAFFIN:OLEFIN ALKYLATION PROCESS

[75] Inventors: Kenneth J. Del Rossi, Woodbury, N.J.; Albin Huss, Jr., Chadds Ford, Pa.

[73] Assignee: Mobil Oil Corporation, Fairfax, Va.

[21] Appl. No.: 719,277

[22] Filed: Jun. 21, 1991

[51] Int. Cl.$^5$ ............................................. C07C 2/62
[52] U.S. Cl. .................................. 585/725; 585/722; 585/724; 585/730
[58] Field of Search ............... 585/722, 723, 724, 725, 585/730

[56] References Cited

U.S. PATENT DOCUMENTS

| | | | |
|---|---|---|---|
| 2,406,954 | 9/1946 | Linn | 585/724 |
| 2,615,908 | 10/1952 | McCaulay et al. | 260/438 |
| 3,531,546 | 9/1970 | Hervert | 260/683.51 |
| 3,778,489 | 12/1973 | Parker et al. | 260/683.43 |
| 3,795,712 | 3/1974 | Torck et al. | 260/671 |
| 3,856,764 | 12/1974 | Throckmorton et al. | 260/82.1 |
| 3,865,896 | 2/1975 | McCoy et al. | 585/725 |
| 3,979,476 | 9/1976 | Kemp | 585/724 |
| 4,025,577 | 5/1977 | Siskin et al. | 260/683.51 |
| 4,085,381 | 12/1977 | Jay et al. | 585/724 |
| 4,094,924 | 6/1978 | Siskin et al. | 260/683.51 |
| 4,426,545 | 1/1984 | Kremer | 585/724 |
| 4,472,268 | 9/1984 | Olah | 585/725 |
| 4,636,488 | 1/1987 | Imai et al. | 502/172 |
| 4,646,488 | 3/1987 | Burns | 52/94 |
| 4,938,935 | 7/1990 | Audeh et al. | 423/240 |
| 4,938,936 | 7/1990 | Yan | 423/240 |
| 4,985,220 | 1/1991 | Audeh et al. | 423/240 |
| 5,073,674 | 12/1991 | Olah | 585/725 |

FOREIGN PATENT DOCUMENTS

| | | | |
|---|---|---|---|
| 0243923 | 3/1987 | Fed. Rep. of Germany | 585/725 |
| 0271322 | 8/1989 | Fed. Rep. of Germany | 585/725 |

OTHER PUBLICATIONS

"Alkylation of Isobutane with $C_4$ Olefins", 27 *Ind. Eng. Chem. Res.*, 381-397 (1988).

"*Handbook of Petroleum Refining Processes*", 23-28, (R. A. Meyers, ed., 1986).

Primary Examiner—Asok Pal
Attorney, Agent, or Firm—Alexander J. McKillop; Dennis P. Santini; Robert B. Furr, Jr.

[57] ABSTRACT

The invention provides an isoparaffin:olefin alkylation catalyst composition and a process employing the same, wherein the catalyst composition comprises from about 10 to about 90 percent of at least one acid selected from the group consisting of hydrofluoric acid and the halogen-substituted sulfonic acids, together with from about 10 to about 90 weight percent of an additive having the formula $R-(NO_2)_n$, wherein R is an alkyl, aromatic, alkyl halide or halide-substituted aromatic group having from about 1 to about 30 carbon atoms.

10 Claims, No Drawings

LIQUID ACID ALKYLATION CATALYST AND ISOPARAFFIN:OLEFIN ALKYLATION PROCESS

CROSS-REFERENCE TO RELATED APPLICATIONS

This Application is related by disclosure of similar subject matter to the following U.S. patent applications:
Ser. No. 07/719,276, pending,
Ser. No. 07/720,124, pending
Ser. No. 07/719,274, pending
Ser. No. 07/719,278, pending
Ser. No. 07/720/125, and
Ser. No. 07/719/879 pending,
all filed on even date herewith.

FIELD OF THE INVENTION

The present invention relates to the art of catalytic alkylation. More specifically, the invention relates to a liquid alkylation catalyst and an isoparaffin:olefin alkylation process. Particularly, the invention provides a liquid alkylation catalyst composition which avoids many of the safety and environmental concerns associated with hydrofluoric acid, particularly with concentrated hydrofluoric acid.

BACKGROUND OF THE INVENTION

Alkylation is a reaction in which an alkyl group is added to an organic molecule. Thus an isoparaffin can be reacted with an olefin to provide an isoparaffin of higher molecular weight. Industrially, the concept depends on the reaction of a $C_2$ to $C_5$ olefin with isobutane in the presence of an acidic catalyst producing a so-called alkylate. This alkylate is a valuable blending component in the manufacture of gasolines due not only to its high octane rating but also to its sensitivity to octane-enhancing additives.

Industrial alkylation processes have historically used concentrated hydrofluoric or sulfuric acid catalysts under relatively low temperature conditions. Acid strength is preferably maintained at 88 to 94 weight percent by the continuous addition of fresh acid and the continuous withdrawal of spent acid. As used herein, the term "concentrated hydrofluoric acid" refers to an essentially anhydrous liquid containing at least about 85 weight percent HF.

Hydrofluoric and sulfuric acid alkylation processes share inherent drawbacks including environmental and safety concerns, acid consumption, and sludge disposal. For a general discussion of sulfuric acid alkylation, see the series of three articles by L. F. Albright et al., "Alkylation of Isobutane with $C_4$ Olefins", 27 *Ind. Eng. Chem. Res.*, 381-397, (1988). For a survey of hydrofluoric acid catalyzed alkylation, see 1 *Handbook of Petroleum Refining Processes* 23-28 (R. A. Meyers, ed., 1986).

Hydrogen fluoride, or hydrofluoric acid (HF) is highly toxic and corrosive. However, it is used as a catalyst in isomerization, condensation, polymerization and hydrolysis reactions. The petroleum industry used anhydrous hydrogen fluoride primarily as a liquid catalyst for alkylation of olefinic hydrocarbons to produce alkylate for increasing the octane number of gasoline. Years of experience in its manufacture and use have shown that HF can be handled safely, provided the hazards are recognized and precautions taken. Though many safety precautions are taken to prevent leaks, massive or catastrophic leaks are feared primarily because the anhydrous acid will fume on escape creating a vapor cloud that can be spread for some distance. Previous workers in this field approached this problem from the standpoint of containing or neutralizing the HF cloud after its release.

U.S. Pat. Nos. 4,938,935 and 4,985,220 to Audeh and Greco, as well as U.S. Pat No. 4,938,936 to Yan teach various methods for containing and/or neutralizing HF acid clouds following accidental releases.

But it would be particularly desirable to provide an additive which decreases the cloud forming tendency of HF without compromising its activity as an isoparaffin:olefin alkylation catalyst. Solvents and complexing agents for hydroflouric acid complexes have, in the past, been disclosed for various purposes as noted in the following references.

U.S. Pat. No. 2,615,908 to McCaulay teaches thioether-HF-copper complex compounds and a method for preparing the same. Potential uses for the thioether-HF-copper composition compounds are listed from column 6, line 55 through column 8 at line 3. The method is said to be useful for purifying HF-containing vent gases from an industrial HF alkylation plant. See column 7, lines 10-24.

U.S Pat. No. 3,531,546 to Hervert discloses a HF-$CO_2$ catalyst composition which is said to be useful for alkylation as well as olefin isomerization.

U.S. Pat. No. 3,795,712 to Torck et al. relates to acid catalysts comprising a Lewis acid, a Bronsted acid, and a sulfone of the formula $R-SO_2-R'$, where R and R' are each separately a monovalent radical containing from 1 to 8 carbon atoms or form together a divalent radical having from 3 to 12 carbon atoms.

U.S. Pat. No. 3,856,764 to Throckmorton et al. teaches an olefin polymerization catalyst comprising (1) at least one organoaluminum compound, (2) at least one nickel compound selected from the class consisting of nickel salts of carboxylic acids, organic complex compounds of nickel, or nickel tetracarbonyl and (3) at least one hydrogen fluoride complex prepared by complexing hydrogen fluoride with a member of the class consisting of ketones, ethers, esters, alcohols, nitriles, and water.

U.S. Pat. No. 4,636,488 discloses an anhydrous nonalcoholic alkylation catalyst comprising a mixture of a mineral acid and an ether in proportions of from about 50 to about 99 weight percent of mineral acid and from about 1 to about 50 weight percent of ether. Useful mineral acids include HF; see column 4 at lines 56-60.

Promoters such as alcohols, thiols, water, ethers, thioethers, sulfonic acids, and carboxylic acids are disclosed in combination with strong Bronsted acids such as HF, fluorosulfonic and trihalomethanesulfonic acids in U.S. Pat. No. 3,778,489 to Parker et al. The promoters are said to modify the activity of the strong Bronsted acids for alkylation.

The foregoing references are incorporated by reference as if set forth at length herein, particularly for the details of HF alkylation process operation. In view of the increasing safety and environmental concerns surrounding the cloud-forming tendency of hydrofluoric acid, providing an additive to mitigate HF cloud formation without disturbing the catalytic properties of hydrofluoric acid for isoparaffin:olefin alkylation would clearly be a major advance in the art. Thus one object of the present invention is to provide a catalyst composition which can be substituted for concentrated hydrofluoric acid in a conventional riser-type hydrofluoric acid isoparaffin:olefin alkylation process unit. A further object of the invention is to provide a catalyst composition which provides sufficient acid strength to minimize loss of throughput capacity upon replacing concentrated hydrofluoric acid with the catalyst composition of the invention in an industrial riser-type hydrofluoric acid isoparaffin:olefin alkylation process.

SUMMARY OF THE INVENTION

In accordance with the present invention, it has been found that certain nitrogen-containing additives suppress the vapor-forming tendency of strong acids such as HF but, surprisingly, have only minor effects on their isoparaffin:olefin alkylation activity. The additives of the invention have further been found to offer desirable process flexibility in that a catalyst composition of the invention containing a nitroalkane additive may readily be used in an industrial riser-type hydrofluoric acid alkylation process unit as a substitute for the hydrofluoric acid catalyst. The mechanism underlying the unusual behavior of the nitroalkanes is not well understood; indeed, this development contradicts the reasonable expectation that dilution would degrade HF catalyst performance. The result is particularly surprising because years of industrial experience have proven that maintaining acid strength in commercial HF alkylation process units is critical to alkylate product quality, with loss of acid strength precipitating immediate degradation in alkylate product quality.

The invention provides, in a first aspect, an alkylation catalyst composition comprising from about 10 to about 90 weight percent of at least one acid selected from the group consisting of hydrofluoric acid and the halogen-substituted sulfonic acids, together with from about 10 to about 90 weight percent of an additive having the formula $R\text{-}(NO_2)_n$, wherein R is an alkyl, aromatic, alkyl halide or halide-substituted aromatic group having from about 1 to about 30 carbon atoms, preferably from about 1 to about 10 carbon atoms, more preferably from about 1 to about 6 carbon atoms, wherein n is from 1 to 3. If R is an alkyl halide or a halide-substituted aromatic, R may be partially or fully substituted. Examples of useful halogenated sulfonic acids include chlorosulfonic, fluorosulfonic, difluoromethanesulfonic, trifluoromethanesulfonic, and perfluoroalkanesulfonic acids.

The invention further provides, in a second aspect, a process for alkylating an isoparaffin with an olefin comprising contacting at least one isoparaffin and at least one olefin with an alkylation catalyst composition comprising from about 10 to about 90 weight percent of at least one acid selected from the group consisting of hydrofluoric acid and the halogen-substituted sulfonic acids, together with from about 10 to about 90 weight percent of an additive having the formula $R\text{-}(NO_2)_n$, wherein R is an alkyl, aromatic, alkyl halide or halide-substituted aromatic group having from about 1 to about 30 carbon atoms, preferably from about 1 to about 10 carbon atoms, more preferably from about 1 to about 6 carbon atoms, wherein n is from 1 to 3. If R is an alkyl halide or a halide-substituted aromatic, R may be partially or fully substituted.

DETAILED DESCRIPTION

Feedstocks

Feedstocks useful in the present alkylation process include at least one isoparaffin and at least one olefin. The isoparaffin reactant used in the present alkylation process has from about 4 to about 8 carbon atoms. Representative examples of such isoparaffins include isobutane, isopentane, 3-methylhexane, 2-methylhexane, 2,3-dimethylbutane and 2,4-dimethylhexane.

The olefin component of the feedstock includes at least one olefin having from 2 to 12 carbon atoms. Representative examples of such olefins include butene-2, isobutylene, butene-1, propylene, ethylene, hexene, octene, and heptene, merely to name a few. The preferred olefins include the $C_4$ olefins, for example, butene-1, butene-2, isobutylene, or a mixture of one or more of these $C_4$ olefins, with butene-2 being the most preferred. Suitable feedstocks for the process of the present invention are described in U.S. Pat. No. 3,862,258 to Huang et al. at column 3, lines 44-56, the disclosure of which is incorporated by reference as if set forth at length herein.

The molar ratio of isoparaffin to olefin is generally from about 1:1 to about 100:1, preferably from about 1:1 to about 50:1, and more preferably from about 5:1 to about 20:1.

Catalyst Composition

The catalyst composition of the present invention comprises from about 10 to about 90 weight percent of at least one acid selected from the group consisting of hydrofluoric acid and the halogen-substituted sulfonic acids, and from about 10 to about 90 weight percent of an additive having the formula $R\text{—}(NO_2)_n$, wherein R is an alkyl, aromatic, alkyl halide or halide-substituted aromatic group having from about 1 to about 30 carbon atoms, preferably from about 1 to about 10 carbon atoms, more preferably from about 1 to about 6 carbon atoms, wherein n is from 1 to 3. If R is an alkyl halide or a halide-substituted aromatic, R may be partially or fully substituted.

The alkylation catalyst composition of the invention preferably comprises from about 10 to about 60 weight percent additive, more preferably from about 20 to about 50 weight percent additive, with the substantial balance of the catalyst composition comprising the acid. The catalyst composition of the invention is preferably free of intentionally added water, and still more preferably, is anhydrous.

Process Conditions

The catalyst composition of the present invention may be readily substituted for the concentrated hydrofluoric acid catalyst in an existing hydrofluoric acid alkylation process without substantial equipment modifications. Accordingly, the conversion conditions for the process of the present invention resemble those of typical commercial hydrofluoric acid alkylation processes. The present alkylation process is suitably conducted at temperatures of from about 10° to about 100° C., preferably from about 20° to about 80° C., and more preferably below about 25° C. to avoid undesirable side reactions. Pressure is maintained to ensure a liquid phase in the alkylation reaction zone, typically falling within the range of from about 20 to about 1200 psig, and preferably are within the range of from about 50 to about 500 psig. Olefin feed rates can vary from 0.01 to 10 weight hourly space velocity (WHSV), and are preferably from about 0.05 to about 5 WHSV. Contact times for isoparaffin:olefin feed with the catalyst composition of the present invention can range from about 0.1 second to about 100 minutes, and more preferably are from about 10 seconds to about 20 minutes.

The alkylation reaction may be conducted in any suitable reactor vessel, for example, a stirred tank or a riser-type reactor. While the scope of the present invention is not limited by reactor configuration, the catalyst composition of the invention may readily be used in existing conventional riser-reactor hydrofluoric acid isoparaffin:olefin alkylation process units as a substitute for concentrated hydrofluoric acid.

The additive component of the catalyst composition may be injected directly into the alkylation process unit. Alternatively, the additive component may be mixed with either the hydrocarbon charge or the fresh and/or circulating acid component of the catalyst composition. Downstream from the alkylation reaction zone, the additive component is preferably separated from the alkylate product stream, mixed with fresh acid and/or circulating catalyst, and recycled to the alkylation reaction zone. The particular separation technique selected, however, depends at least in part upon the size and characteristic chemistry of the R groups contained in the additive. For instance, nitromethane is only sparingly soluble in the alkylate product while 1-nitropropane is appreciably soluble and requires the appropriate separation steps to purify the alkylate product.

In a typical commercial embodiment, the effluent stream from the alkylation reaction zone is separated, e.g., decanted, into an alkylate-rich hydrocarbon stream and an acid recycle stream. The alkylate-rich hydrocarbon stream is typically fractionated further to provide an isoparaffin recycle stream to the alkylation reaction zone. In the present invention, the preferred method for recycling the nitroalkane additive to the alkylation reaction zone varies with the particular nitroalkane employed. Decanting the alkylation reaction zone effluent to separate alkylate-rich hydrocarbon from the HF/nitromethane mixture has been found to yield relatively pure hydrocarbon and HF/nitromethane streams. But in contrast, nitroalkanes having two or more carbon atoms, for example, nitropropane, are partitioned between the alkylate-rich hydrocarbon stream and the HF/nitroalkane streams upon decantation, and the resulting hydrocarbon stream must be further purified to recover the nitroalkane. The extent of partitioning increases with increasing carbon number of the nitroalkane, and is clearly evident with nitropropane (3 carbon atoms) and heavier nitroalkanes (having 4 or more carbon atoms). Suitable purification techniques include distillation of the alkylate from the nitropropane as well as solvent extraction of the nitropropane from the alkylate with a suitable solvent, for example, a polar solvent such as methanol.

EXAMPLES

The following Examples 1-6 demonstrate the effectiveness of the catalyst composition of the invention for catalyzing isoparaffin:olefin alkylation. Example 1 demonstrates the well-known effectiveness of anhydrous HF as an isoparaffin:olefin alkylation catalyst and is presented for comparison to evaluate the effectiveness of various nitrogen-containing additives (Examples 2-6).

EXAMPLE 1

Comparative

Anhydrous HF (40 grams, obtained from Matheson Chemical Company of Bridgeport, N.J.) was condensed into a clean, dry autoclave (1000 cc). Isobutane (100 grams) was added, and the autoclave was stirred at C1500 rpm. The autoclave was brought to room temperature (22° C., 71° F.) and pressurized to 100 psig. A pre-mixed 10:1 weight:weight mixture of isobutane:2-butene feed (obtained from Matheson Chemical Company) was added at a rate of 250 cc/hour for 2 hours under autogeneous pressure for a total isobutane:2-butene charge of 500 cc. A 8°-12° F. (4°-7° C.) temperature rise was observed during feed addition resulting in an average reaction temperature of 79°-83° C. (26°-28° F.). The autoclave was sampled (300 cc) immediately after feed addition was complete. The sample was flashed at room temperature and quenched with a chilled water trap. Samples of the liquid and gas products were analyzed by capillary GC (60m DB-1 column). The results of Example 1 are shown in the table below.

EXAMPLE 2

HF/Nitromethane

Ten (10) grams of chilled nitromethane was added to a clean, dry autoclave (1000 cc). The autoclave was sealed, cooled with a dry ice/acetone bath and placed under vacuum. Anhydrous HF (40 grams, obtained from Matheson Chemical Company of Bridgeport, N.J.) was then condensed into the autoclave. Isobutane (100 grams) was added, and the autoclave was stirred at 1500 rpm. The autoclave was brought to room temperature (22° C., 71° F.) and pressurized to 100 psig. A pre-mixed 10:1 weight:weight mixture of isobutane:2-butene feed (obtained from Matheson Chemical Company) was added at a rate of 250 cc/hour for 2 hours under autogeneous pressure for a total isobutane:2-butene charge of 500 cc. A 10°-15° F. (5°-8° C.) temperature rise was observed during feed addition resulting in an average reaction temperature of 27°-30° C. (80°-85° F). The autoclave was sampled (300 cc) immediately after feed addition was complete. The sample was flashed at room temperature and quenched with a chilled water trap. Samples of the liquid and gas products were analyzed by capillary GC (60m DB-1 column). The results of Example 2 are shown in the table below.

EXAMPLE 3-6

The procedure of Example 2 was repeated with a higher concentration of nitromethane $C_{(Example\ 3)}$, HF/1-nitropropane (Example 4), HF/diethanolamine (Example 5), and HF/pyridine (Example 6). The table below summarizes the results from of these experiments, showing that while the nitroalkanes (e.g., nitromethane and 1-nitropropane) provided effective isoparaffin:olefin alkylation catalysis in the presence of HF, other nitrogen-containing organics, (e.g., diethanolamine and pyridine) proved largely ineffective as alkylation catalyst additives for HF. Thus while it is clear that the catalyst compositions of the invention catalyze isoparaffin:olefin alkylation, the reasons why this particular class of compounds exhibit these unusual properties remain unclear. Accordingly, the scope of the present invention is not to be limited by any recitation of theory, but only by the scope of the appended claims.

TABLE

|  | Example 1 | Example 2 | Example 3 | Example 4 | Example 5 | Example 6 |
|---|---|---|---|---|---|---|
| Catalyst | HF | HF/CH$_3$NO$_2$ | HF/CH$_3$NO$_2$ | HF/CH$_3$(CH$_2$)$_2$NO$_2$ | HF/DEA | HF/Pyridine |
| Appearance | Fuming | Liquid | Liquid | Liquid | Liquid | Liquid |
| HF/Additive Ratio (mol/mol) | — | 12/1 | 6/1 | 6.5/1 | 21/1 | 9/1 |
| Alkylate Product, wt % |  |  |  |  |  |  |
| C$_5$-C$_7$ | 5.5 | 5.2 | 5.4 | 5.8 | 20.1 | — |
| C$_8$ | 88.1 | 89.7 | 85.6 | 86.1 | 48.8 | — |
| C$_9$+ | 6.4 | 5.1 | 9.0 | 8.1 | 31.1 | — |
| TMP/DMH | 9.2 | 8.6 | 7.7 | 8.6 | 2.5 | — |
| Olefin Conv.,% | 99.9 | 99.5 | 99.2 | 98.1 | 91.2* | 47.1* |

*Significant quantities of butyl fluoride detected.

Pure HF boils at 19.7° C. and fumes violently upon exposure to moist air. The HF/CH$_3$NO$_2$ mixtures tested (12/1 and 6/1 mol/mol) as well as the HF/CH$_3$(CH$_2$)$_2$NO$_2$ mixtures were stable liquids which fumed mildly in air. The physical appearance of the HF/nitroalkane mixtures indicated that the vapor pressure of HF had been significantly reduced. However, alkylation performance was only slightly diminished upon adding nitroalkanes to HF in HF/additive molar ratios as high as 6/1. The ratio of high octane trimethylpentanes to lower octane dimethylhexanes (TMP/DMH) decreased slightly from 9.2 with a pure HF catalyst to 7.7 with a 6/mol/mol HF/CH$_3$NO$_2$ catalyst composition. Further, the amount of heavy C$_9$+ alkylate increased from 6.4 wt % to only 9.0 wt % with the 6/1 catalyst composition. Similar results were observed with 1-nitropropane. These results are unexpected because the molar ratio of HF/CH$_3$NO$_2$ was as low as 6/1, and because basic nitrogen compounds such as pyridine and diethanolamine (DEA) dramatically reduce HF alkylation performance at significantly higher HF/additive molar ratios as shown in the table above.

Changes and modifications in the specifically described embodiments can be carried out without departing from the scope of the invention which is intended to be limited only by the scope of the appended claims.

What is claimed is:

1. A process for alkylating an isoparaffin with an olefin comprising effecting reaction of isoparaffin and olefin with an alkylation catalyst composition comprising from about 10 to about 90 percent of at least one acid selected from the group consisting of hydrofluoric acid and the halogen-substituted sulfonic acids, together with from about 10 to about 90 weight percent of an additive having the formula R—(NO$_2$), wherein R is an alkyl, aromatic, halide-substituted alkyl or halide-substituted aromatic group having from about 1 to about 30 carbon atoms.

2. The process of claim 1 wherein R is selected from alkyl, aromatic, halogen-substituted alkyl, and halogen-substituted aromatic groups having from about 1 to about 10 carbon atoms.

3. The process of claim 2 wherein R is selected from alkyl, aromatic, halogen-substituted alkyl, and halogen-substituted aromatic groups having from about 1 to about 6 carbon atoms.

4. The process of claim 3 wherein said additive is selected from the group consisting of nitromethane and 1-nitropropane.

5. The process of claim 1 comprising from about 10 to about 60 weight percent of an additive having the formula R—(NO$_2$).

6. The process of claim 5 comprising from about 20 to about 50 weight percent of an additive having the formula R—(NO$_2$).

7. The process of claim 1 further comprising contacting said isoparaffin and olefin with said alkylation catalyst composition in a riser reactor.

8. A process for alkylating an isoparaffin with an olefin comprising effecting reaction of isoparaffin and olefin with an alkylation catalyst composition comprising from about 10 to about 90 weight percent hydrofluoric acid and from about 10 to about 90 weight percent of an additive having the formula R—(NO$_2$), wherein R is an alkyl, halide-substituted alkyl aromatic or halogenated aromatic group having about 1 to about 30 carbon atoms, wherein said alkylation catalyst composition is a substantially nonfuming liquid at atmospheric temperature and pressure and wherein said process produces an alkylate product from a given feedstock having a ratio of trimethylpentanes to dimethylhexanes of at least 84 percent of the ratio of trimethylpentanes to dimethylhexanes of the alkylate product produced by contacting said given feedstock with neat HF under like conversion conditions.

9. The catalyst composition of claim 8 wherein R is selected from alkyl, aromatic, halogen-substituted alkyl, and halogen-substituted aromatic groups having from about 1 to about 10 carbon atoms.

10. The catalyst composition of claim 9 wherein R is selected from alkyl, aromatic, halogen-substituted alkyl, and halogen-substituted aromatic groups having from about 1 to about 6 carbon atoms.

* * * * *